United States Patent [19]
Jones

[11] Patent Number: 5,387,183
[45] Date of Patent: Feb. 7, 1995

[54] MULTI-PLY SUPPORT BELT

[76] Inventor: Robert W. Jones, 9807 Fredericksburg Rd., San Antonio, Tex. 78240

[21] Appl. No.: 81,552

[22] Filed: Jun. 23, 1993

[51] Int. Cl.⁶ ............................................. A61F 5/00
[52] U.S. Cl. .................... 602/19; 128/99.1; 128/100.1; 128/101.1
[58] Field of Search ............. 602/19; 2/44, 92, 371; 450/155; 128/95.1, 96.1, 99.1, 100.1, 101.1

[56] References Cited

U.S. PATENT DOCUMENTS

| | | | |
|---|---|---|---|
| 3,920,008 | 11/1975 | Lehman | 128/96.1 |
| 4,572,167 | 2/1986 | Brunswick | 2/44 X |
| 5,007,412 | 4/1991 | DeWall | 2/44 X |
| 5,040,524 | 8/1991 | Votel et al. | 602/19 |
| 5,111,806 | 5/1992 | Travis | 602/19 |
| 5,148,549 | 9/1992 | Sydor | 2/44 |

FOREIGN PATENT DOCUMENTS

| | | | |
|---|---|---|---|
| 119478 | 9/1984 | European Pat. Off. | 602/19 |
| 2243787 | 11/1991 | United Kingdom | 602/19 |

Primary Examiner—Stephen R. Crow
Assistant Examiner—Linda C. M. Dvorak
Attorney, Agent, or Firm—Gunn, Lee & Miller

[57] ABSTRACT

A multi-ply, back and abdominal support belt having a generally elastic primary ply, a non-elastic, unyielding secondary ply, and a high tension elastic tertiary ply. The multi-ply belt is further provided with cooperation fasteners and securing elements to hold the elements in cooperative engagement. Reinforcing straps are further attached to the belt to control tension balances.

11 Claims, 7 Drawing Sheets

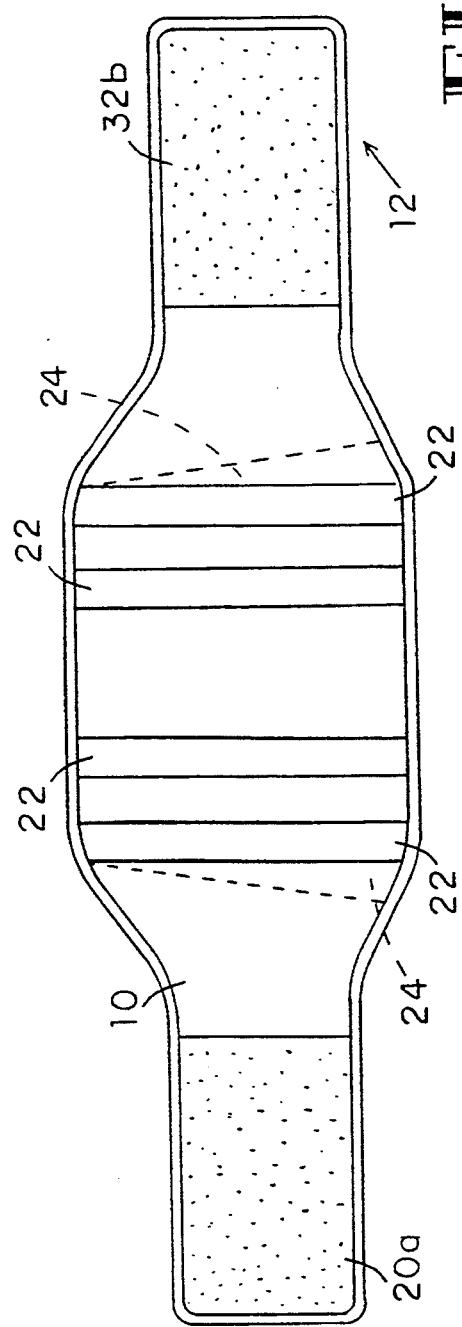

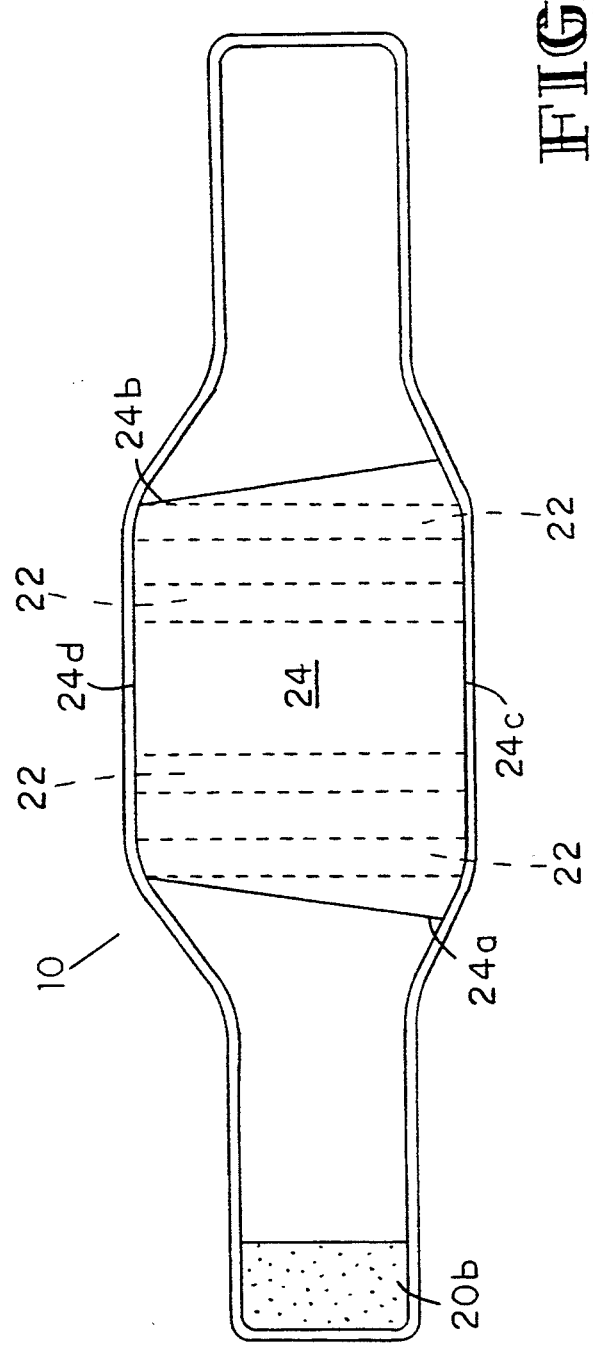

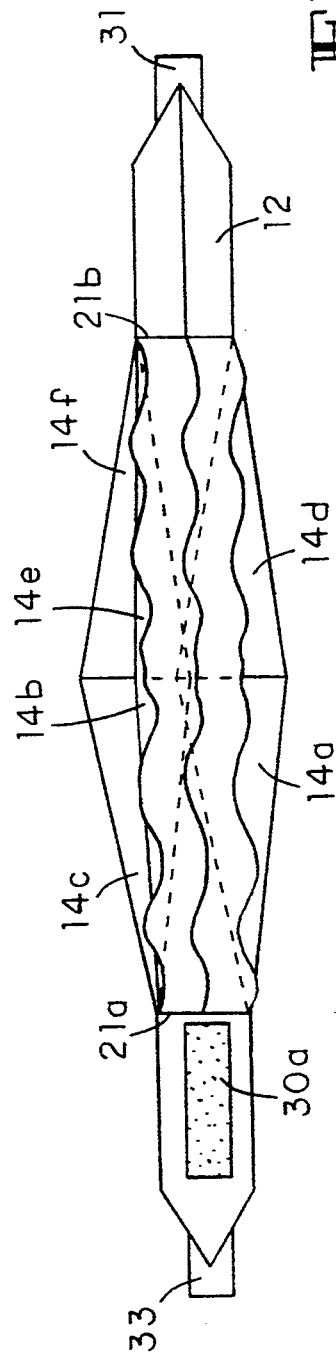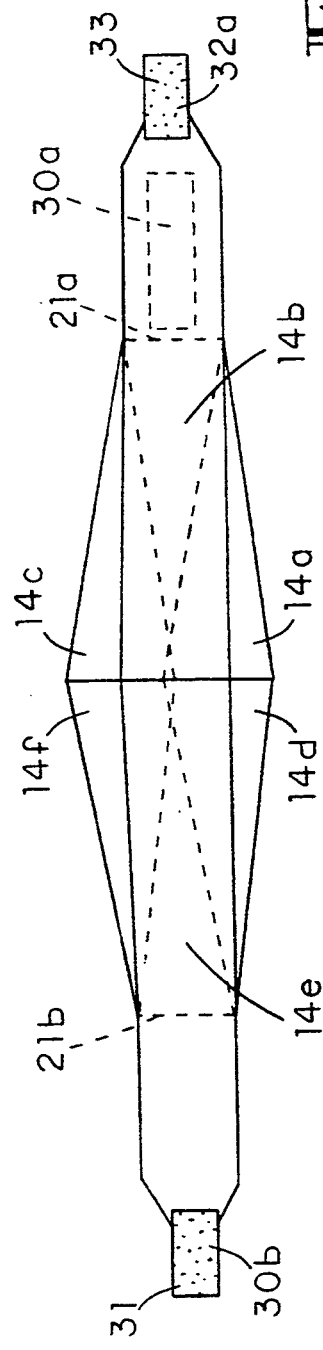

MULTI-PLY SUPPORT BELT

BACKGROUND OF THE INVENTION

1. Field of the Invention

This invention generally relates to support belts worn during heavy lifting for prevention of back related injuries, more specifically to a multi-ply support belt which provides abdominal as well as back support through utilization of elastic as well as non-elastic elements.

2. Background

Our jobs as well as our exercise programs often require extended use of the back. Heavy lifting as well as routine prolonged manipulation of the back often prompts or promotes various back and/or abdominal injuries. The stress of lifting, holding, and transporting weight as well as the stress of normal but extended movement, including the impact of each step taken, is transmitted to and along the spine.

The continuous, high level of stress encountered and endured by the back helps explain the frequency of back and abdominal injuries. These back and abdominal injuries are usually precipitated by weak abdominal muscles, weak back extensor muscles, excessive or diminished lumbar (lower back) curve, poor posture, and/or use of improper body mechanics. In order to protect against and avoid typical back and abdominal injuries, strengthening of spinal and abdominal muscles is recommended. Although strengthening of the spinal and abdominal muscles may be accomplished physically through exercise, strengthening may be physically or artificially achieved through use of a support belt. The required features of a support belt for strengthening and support of the lower back muscles, however, differ from those required for support of the abdominal muscles.

A support belt may act to strengthen and/or support the abdominal muscles. In order to accomplish such strengthening or support, however, the belt must be positioned across the lower abdominal area and must provide non-elastic, unyielding support. This holds and lifts the abdominal muscles up and in and contains the lower abdominal muscles while relieving stress on the back. In turn, this action supports and strengthens the abdominal muscles while adding extra support to the lower back through encasing the lower back with the abdominal muscles.

A support belt may also act to strengthen and/or support the lower back and sacral area. This strengthening or support is accomplished through positioning of the belt generally across the pelvic or lower abdominal area but, unlike a belt which supports the abdominal muscles, the belt must be elastic. Elasticity allows for natural retention of the lower back's curve and sacral area's tilt permitting proper body mechanics and posture which in turn contribute heavily to strengthening and support of the lower back area.

One common type of support belt is the standard weight lifting belt. These belts, as well as most types of support belts, are wide in back with a gradual slope toward a narrower front. The weight lifter belt, however, is usually made of a non-stretch material ranging from ¼" to ½" thick. Although this belt may help support the abdominal muscles, it does not support the back or sacral area.

The typical weight lifting belt is unyielding to normal movements and curvatures of the human body. The sacral area, for instance, has a predominant tilt, particularly in men. This tilt contributes to the strengthening and support of the sacral and lower back areas.

Other support belts utilize elastic for more effective support of the lower back and sacral area. Although more commonly used for job-related lifting, elastic support belts often resemble the leather weight lifting belt in shape but are made of heavy elastic which succumbs to limited but natural movements and curvatures of the body. This allows the sacral area to maintain its natural tilt and the lower back area to maintain its natural curvature for more effective strengthening and support.

In order to achieve greater support of the lower back and sacral area, a composite belt exists and consists of two sub-belts which are attached and function as one. A main elastic sub-belt typically has the standard shape of most support belts while a smaller elastic sub-belt consisting of one or more highly elastic bands extends around the midline of the main belt. This composite belt offers greater support for the lower back and sacral area but offers little, if any, support for the abdominal muscles. The abdominal area requires unyielding or rigid support which cannot be acquired from an elastic belt alone.

Several standard elastic support belt designs incorporate use of shoulder straps. These straps, however, offer no additional support and serve only to provide a means for supporting the belt while unfastened.

In addition to support belts found in the weight lifting and industrial fields, there are also support belts used exclusively in the medical area. There is a need for effective support of the lower back and abdominal areas for those recovering from back or abdominal injuries as well as back or abdominal surgery. One common therapeutic support belt consists of a standard support belt which incorporates air bladders along the inside of the belt. The wearer inflates or deflates the bladders for the desired consistency of support. Although some therapeutic belts could be used in the industrial and weight lifting fields, such belts are often cost prohibitive.

While many types of support belts exist, none provide strengthening and support for both the abdominal as well as lower back and sacral areas. None possess the versatility to effectively and efficiently provide the needed support in more than one field of use. The present invention addresses both of these needs through a support belt, appropriate for use in the medical, industrial, and exercise fields, which provides support for the abdominal as well as lower back and sacral areas.

SUMMARY OF THE INVENTION

The present invention is a multi-ply support belt for use in a variety of fields for support of the abdominal as well as lower back and sacral areas. The belt consists of a primary elastic ply, a narrower secondary non-elastic ply, and a tertiary high tension elastic ply which is attached to the back of the secondary ply in a manner such that the secondary ply is gathered and therefore initially non-tensioned in a first related position. The secondary and tertiary plies are permanently attached to the primary ply midway between opposing ends of the primary ply. The ends of the secondary ply are adjustably attached to the primary ply after the secondary ply is extended to its limit or point of tension. The present invention successfully combines elastic primary and tertiary ply for support of the lower back and sacral areas with a non-elastic, non-yielding secondary ply for full support of the abdominal muscles.

It is an object of the present invention to provide a support belt which, by incorporating elastic as well as non-elastic components, permits strengthening and support of both the lower back and abdominal muscles.

It is also an object of the present invention to provide a support belt which, by incorporating a feature which allows for insertion of a heat moldable form, may be utilized in the medical as well as industrial field.

Another object of the present invention is to provide a support belt which provides a stretch limiting feature through use of a non-elastic secondary ply.

Another object of the present invention is to provide a support belt which while supporting the abdominal and spinal muscles, helps to simultaneously strengthen them.

Other purposes and advantages will become apparent from the following description in light of the attached drawings.

BRIEF DESCRIPTION OF THE DRAWINGS

FIG. 6 illustrates a rear elevation view of the primary ply of the present invention showing the outer surface.

FIG. 7 illustrates a front elevation view showing the inner surface of the primary ply of the present invention.

FIG. 8 illustrates a rear elevation view of the secondary and tertiary plies of the present invention from their outer surface.

FIG. 9 illustrates a front elevation view of the secondary and tertiary plies of the present invention showing their inner surfaces.

DETAILED DESCRIPTION OF THE PREFERRED EMBODIMENT

In the figures, thickness of the various plies of the present support belt are greatly exaggerated to show the construction details. Further, space between plies is also exaggerated for illustration purposes.

Figure 1:
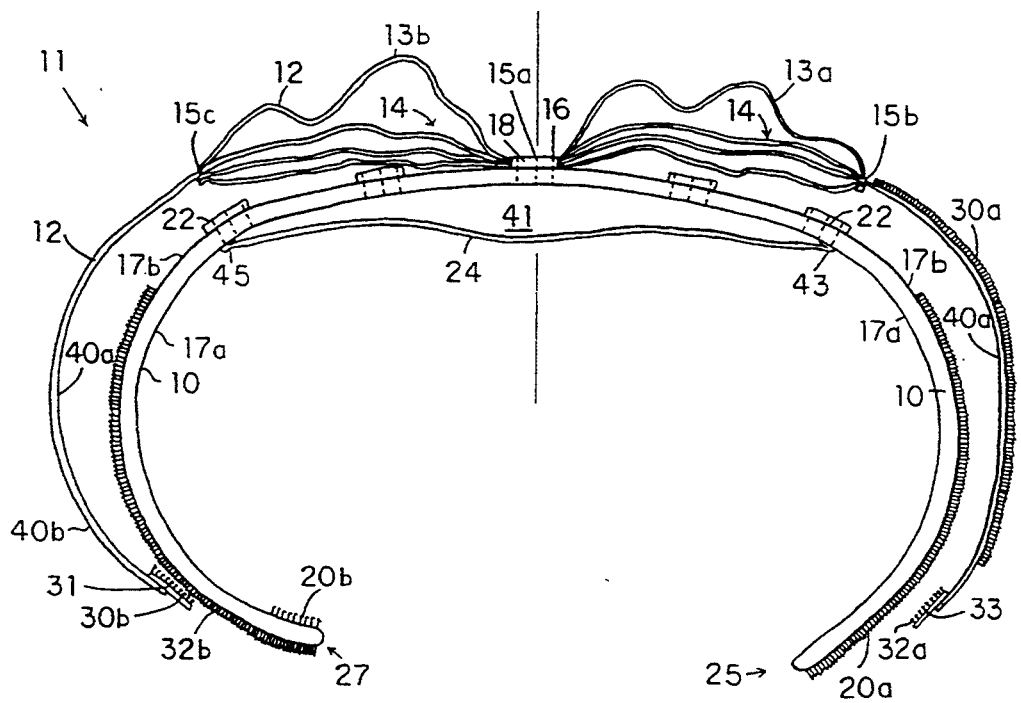
FIG. 1 illustrates a top view of the multi-ply support belt of the present invention in a first "relaxed," non-tensioned position.

FIG. 1 illustrates the multi-ply support belt 11 of the present invention. The generally elastic primary ply 10, the non-elastic secondary ply 12, and the high tension elastic tertiary ply 14 of the present invention are shown assembled and ready for use. Tertiary ply 14 may be made up of two sets of three separate sub-bands as will be discussed below. The secondary 12 and tertiary 14 plies are stitched together along composite seams 16 and secured under the support belt's center rib reinforcement strap 18 at the back section of primary ply 10 for affixation to the primary ply 10. Through this assembly, the present invention is easily utilized for effective support of the abdominal, lower back, and sacral areas.

Primary ply 10 has an inner surface 17a and an outer surface 17b. The primary ply may be composed of a perforated elastic material well known in the art. The elastic is a rubber or extruded latex elastomer. The perforations are generally 1/16" in diameter. An alternative material for the primary ply is an elastic netting or screen-like material which is made of nylon and LYCRA (a trademark for an elastic fiber manufactured by DuPont Company). A preferred netting material would be 86% nylon and 14% LYCRA. The primary ply material has a lower elastic tension than does the tertiary ply as discussed below.

The generally elastic primary ply 10 is retainable around the wearer's body, over the lower abdominal area, by means of a two-part fastener system such as hook and loop fabric (commonly known by the trademark VELCRO). Loop part 20a is affixed to the left end 25, outer surface 17b, and hook part 20b is affixed to right end 27, inner surface 17a. Primary ply 10 also has an additional section 32b of the loop portion of the fastener extending along the outer surface 17b of the primary ply near the right end of ply 10.

Figure 5:
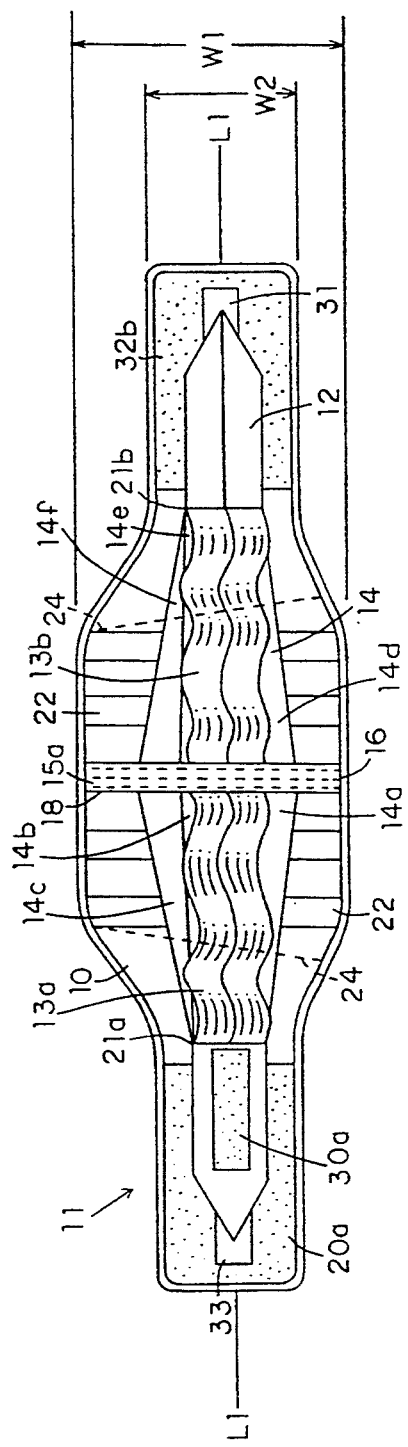
FIG. 5 illustrates the multiplicity belt of the present invention in a rear elevation view in the "relaxed" position, showing the outer surfaces of the belt.

FIG. 1 further illustrates that in addition to center rib reinforcement strap 18 extending along the vertical midline of support belt 11, ply 10 has at least four other vertical rib reinforcement straps 22 attached along the back portion of primary ply 10 and extending vertically or generally perpendicular to the primary belt's longitudinal axis L1 (FIG. 5). Straps 22 are sewn or otherwise securely attached to the outer surface 17b of primary ply 10 and serve to balance any stretching or movement occurring in the elastic material of primary ply 10.

The width variations of the various plies of belt 11 may be noted in FIG. 5. Primary ply 10 has a first width dimension W1 extending along the back portion of primary ply 10 which covers the lower back of the wearer and a second width dimension W2 along the side sections of ply 10 which extends from the back portion of primary ply 10 to the front ends of ply 10. The narrower width side sections generally cover the sides and front of the wearer's body when in use. The narrower width enables the wearer to bend forward and bend to the left and right side with a minimum of discomfort and pinching by the belt 11.

It should be noted in FIG. 1 that in the belt's "relaxed" position a back, middle section of secondary ply 12 has excess material in the form of gathers 13a and 13b. The function of the gathers 13a and 13b will be described in more detail below. Gather 13a is formed by a first connection 15a of secondary ply 12 to center rib 18 by means of seams 16, discussed above, and a first connection 15b of secondary ply 12 to tertiary ply 14 by means of a sewn seam 21a (FIG. 5). Excess non-elastic material between connections 15a and 15b form the ripples of material or gather 13a. In a like manner, gather 13b is formed by the first connection 15a of secondary ply 12 to center rib 18 and a second connection 15c of secondary ply 12 to tertiary ply 14 by means of a sewn seam 21b (FIG. 5). Excess non-elastic material between connection 15a and 15c form the ripples of material or gather 13b. Other well-known means of affixing the secondary ply 10 to tertiary 14 may be employed.

The secondary ply may be composed of a generally non-elastic material such as 100% polypropylene yarn, a textured polyester thread, 100% cotton, 50% polyester-50% cotton, or 100% nylon material. Other materials being lightweight and having the high tensite strength and generally non-elastic characteristics of the above materials may be substituted by one of ordinary skill in the art.

Secondary ply 12 has an inner surface 40a and an outer surface 40b. As will be described below, secondary ply 12 is retainable around the wearer's body by means of hook and loop fasteners. Loop part 30a is affixed to the left side, outer surface 40b and hook part 30b is affixed to the right end, inner surface 40a of secondary ply 12. A further fastener section 33 of secondary ply 12 is formed of a hook part 32a attached on the inner surface 40a at the left end.

As shown in FIG. 1, the preferred embodiment of the present invention has a pocket 41 formed by the attachment of an elastic sheet member 24 to the inner surface 17a of primary ply 10. Sheet member 24 is sewn or otherwise affixed along three edges (right, left and bottom) to ply 10, leaving an opening along the top edge.

The resulting pocket allows for insertion of a heat moldable plastic support or pad for therapeutic use of the present invention. Although not shown in the attached drawings, the present preferred embodiment also envisions a support belt without attachment of an elastic sheet member 24. Utilization of a support belt without the elastic sheet member 24 is primarily envisioned for the industrial field. This option gives the present invention the versatility to function in the medical as well as industrial fields.

Figure 2:
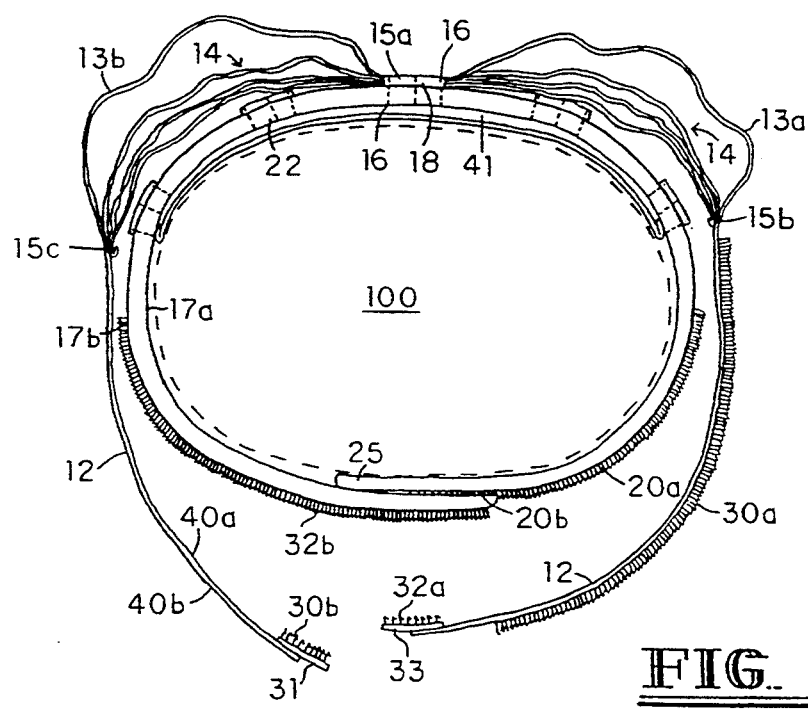
FIG. 2 illustrates a top view of the multi-ply support belt of the present invention wherein the primary ply is extended and tensioned around a wearer.

Turning now to FIG. 2, the first step in a method for providing back and abdominal support is shown.

As previously mentioned, the primary belt is tightly fastened by its fastening means 20a and 20b around the wearer's midsection so that the front of the primary ply falls below the waist and essentially fastens over the wearer's lower abdominal area. Applicant's preferred embodiment utilizes a hook and loop fabric as its fastening means. The loop part of the fabric 20a (shown in FIG. 2) cooperates with its corresponding hook part of the fabric 20b (shown in FIG. 3) to fasten the primary ply 10. Both parts of the hook and loop fastener 20a and 20b are required to effectuate secure fastening of the primary belt 10 around the wearer. The remaining loop part 32b in FIG. 2 cooperates with its' corresponding hook part 32a of the secondary ply 12 for adjustable fastening of the secondary ply 12 to the primary ply 10 as will be discussed.

Thus primary ply 10 is tightly fastened to the wearer's body to provide a compressive and supportive force to the lower back and abdominals. The straps 18 and 22 provide stability and support to the lower back. (In some cases a moldable plastic support or pad is inserted in pocket 41 to give added conforming support.) Many of the support belts known in the prior art simply stop at this point (a single elastic ply) in seeking to solve back and abdominal support and protection. The present invention significantly improves the art by providing a secondary non-elastic, unyielding ply in combination with a third high tension elastic ply.

Figure 3:
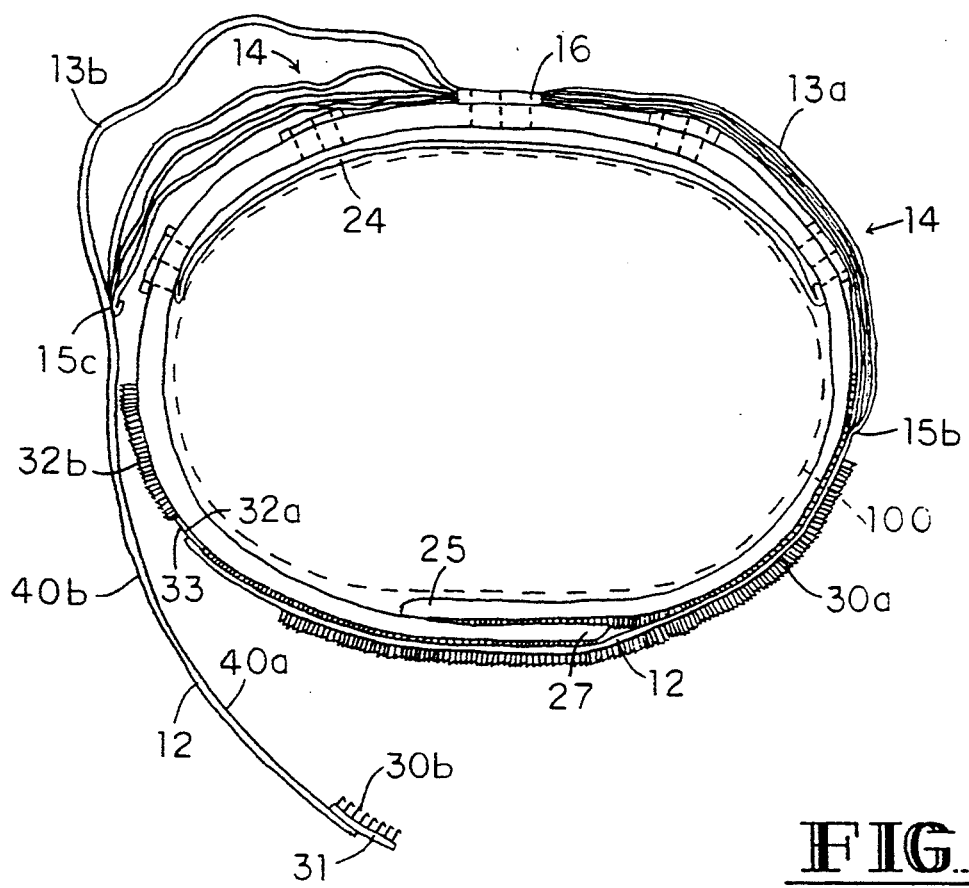
FIG. 3 illustrates a top view of the multi-ply support belt of the present invention wherein one side of secondary ply has been fully extended and fastened to the primary ply.
Figure 4:
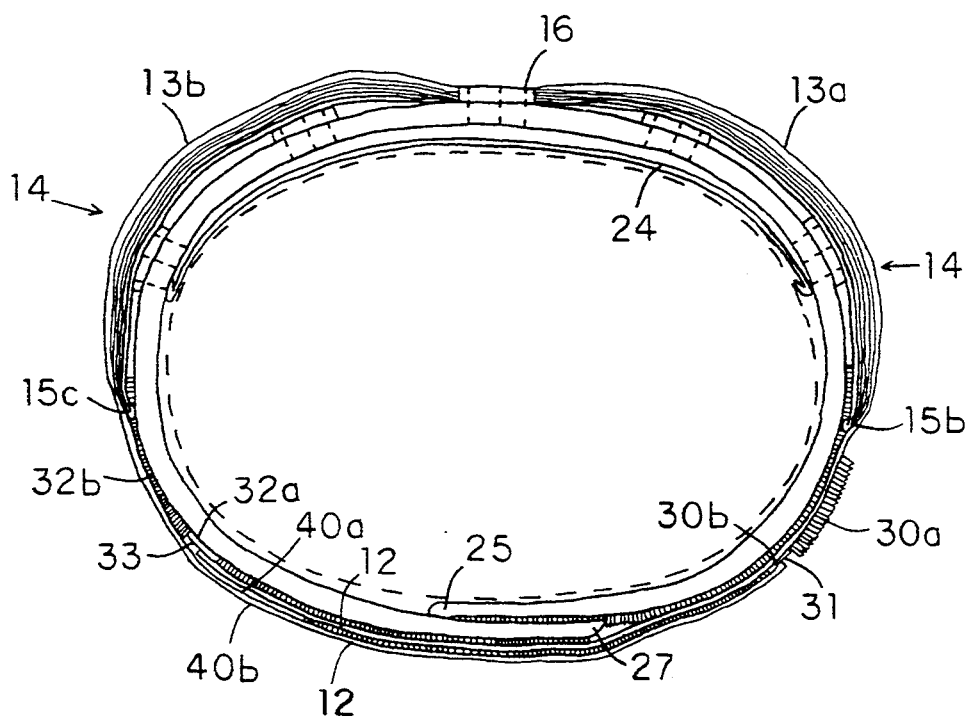
FIG. 4 illustrates a top view of the multi-ply support belt of the present invention in a second "tensioned" position wherein the second, opposite side of the secondary ply also has been fully extended and fastened to the first side outer surface of the secondary ply.

FIGS. 3 and 4 illustrate the next steps in the present method for providing back and abdominal support. In FIG. 3 the left side of secondary ply 12 is pulled to its point of full tension, with all of the excess material or gather 13a removed, and end section 33 is adjustably fastened to the right side of primary ply 10. In FIG. 4, the opposing right side of the secondary ply 12 is then pulled to its point of tension, with all of the excess material or gather 13b removed, and fastened to the loop portion 30a atop the left side of the secondary ply 12 previously fastened to the primary ply 12.

Each side of the secondary ply must be independently pulled to tension as the secondary ply is essentially separated into halves by its attachment to the primary ply midway along its longitudinal dimension. Pulling the non-elastic secondary belt to its point of tension provides the non-elastic, unyielding support required for protection and support of the abdominal muscles.

Movement of the secondary ply to its point of tension to remove gathers 13a and 13b effectuates stretching of the tertiary ply 14 for simultaneous additional high tension, elastic compressive support. Tertiary ply 14 may be composed of an elastic material of rubber or an extruded latex elastomer. However, tertiary ply 14 is made of a material which has a higher elastic tension than the primary ply. Variations of elastic tension in materials may be produced by use of different yarns and varying weave characteristics. Such different degrees of tension in materials is well known to those skilled in the art. Thus, the elastic tertiary ply 14 as well as the elastic primary ply 10 provide two different degrees of tension for protection and compressive support for the lower back and sacral area.

To show the further details of the present invention, FIG. 5 illustrates an elevation view of the multi-ply belt 11 in a flat position. The FIG. 5 view shows the outer surfaces of the belt, or those surfaces not contacting the wearer's body.

FIG. 6 illustrates the primary ply 10 from the outer surface. Straps 22 may be seen affixed to ply 10. Further, the loop parts 20a and 32b of the fastener system may be noted along with width dimension W1 and width dimension W2.

FIG. 7 is intended to show the inner surface of ply 10 with sheet 24 and hook part 20b. It will be remembered that hook part 20b cooperates with loop part 20a to secure the tensioned, stretched primary ply to the wearer's body. Sheet 24 is attached to ply 10 along edges 24a, 24b, and 24c to form pocket 41. Edge 24d is not attached so as to form an opening.

Referring to FIG. 8, the secondary 12 and tertiary 14 plies of the preferred embodiment are illustrated to show their outer surfaces and the cooperative relationship of these plies. The outer surface of the secondary ply 12, as shown in FIG. 4, faces away from the wearer. After securing the primary ply, the wearer pulls the left side of the secondary ply 27 until the gathers 13a of the secondary ply 12 are eliminated and the ply is taut, essentially reaching its point of full extension or tension. A first section of the secondary ply 33 is adjustably fastened to the primary belt through fastening one half of the hook and loop fastener 32a (shown in FIG. 3) to its corresponding half 32b located on the primary ply 10. The wearer then pulls the tab 31 of the second half or right side of the secondary ply until the corresponding part of the secondary ply reaches its point of tension, eliminating all gathers 13b in the secondary ply 12. The hook fastener part 30b located on the inner surface 40a of the secondary ply (shown in FIG. 4) is then fastened to its corresponding loop fastener part 30a. The wearer should fasten the secondary ply such that the end sections of the secondary ply 31 and 33 fall generally across the wearer's pelvic area. In this position, the non-elastic, unyielding secondary ply achieves abdominal support.

Since the secondary 12 and tertiary 14 plies are sewn together at seams 16, 21a and 21b, a pulling action on the secondary ply 12 will cause a stretching result in the high tension elastic tertiary ply 14. As shown in FIG. 8, the tertiary belt may be made up of two sets of three separate high tension elastic sub-bands 14a, 14b, 14c and 14d, 14e, 14f. The separate elastic sub-bands of the tertiary ply are secured along their ends at varying angles for attachment to the secondary ply 12. Spacing of these separate high tension elastic sub-bands allows for efficient and effective support for the lower back and sacral areas.

Figure 10:
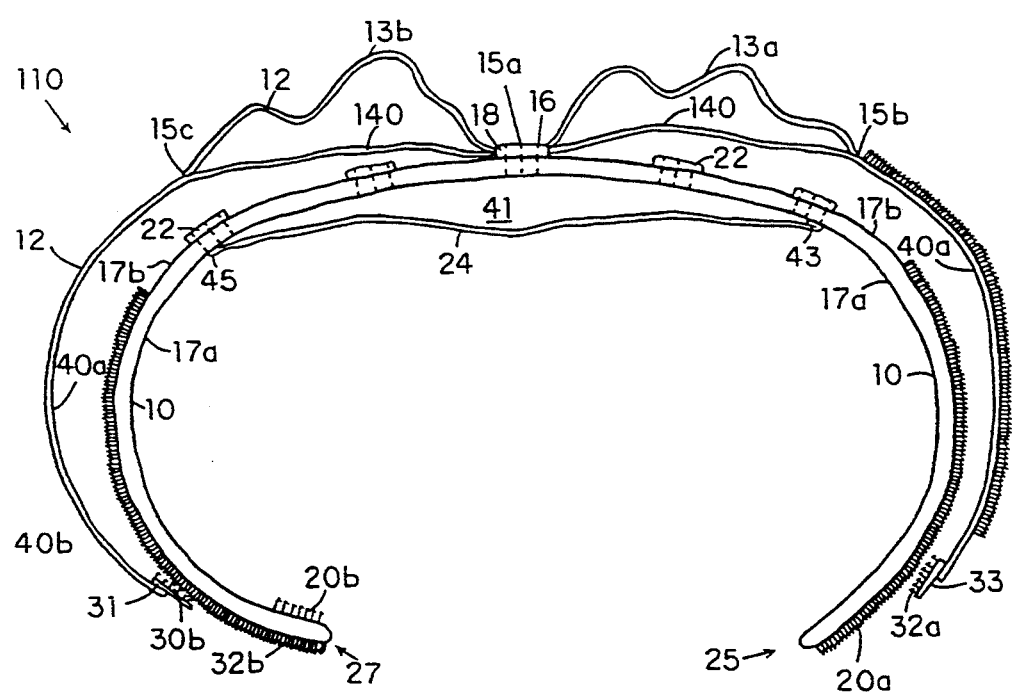
FIG. 10 illustrates a top view of the present invention with a single band tertiary ply.

FIG. 9 illustrates the separate elastic sub-bands of the tertiary ply showing how they overlap to achieve improved support. Sub-band 14a extends diagonally upwardly from the center of the back as it extends to seam 21a. Sub-band 14b is generally horizonal from the center of the back to the side and sub-band 14c extends diagonally downwardly from the center of the back as it extends to seam 21a. In a like manner sub-bands 14d, 14e, and 14f overlap and are oriented as shown in FIG. 9. A single band tertiary ply may be used as shown in FIG. 10. With the single band, as with the sub-bands, the tertiary ply is made of a higher tension elastic than that used in the primary ply as discussed above.

After the wearer has secured the primary ply across the lower abdominal area, the secondary ply and simultaneously the tertiary ply are extended and fastened generally across the wearer's pelvic area. Although the elastic and non-elastic components of the present invention will generally provide support for the lower back and sacral areas respectively, positioning of the present invention is important. Only through appropriate positioning of the present invention will maximum support and strengthening for the lower back, sacral area, and abdominal area be achieved.

While the invention has been described in connection with a preferred embodiment, it is not intended to limit the invention to the particular form set forth, but, on the contrary, it is intended to cover alternatives, modifications, and equivalents, as may be included within the spirit and scope of the invention as defined by the appended claims.

What is claimed is:

1. A multi-ply support belt for back and abdominal support of a wearer's body, said belt comprising:
    an elastic primary ply having a right end and a left end and an outer surface and an inner surface, said inner surface of said primary ply adapted to urge against said wearer's body and provide a first compressional support when said belt is wrapped around said body such that said right end of said primary ply overlaps said left end of said primary ply;
    a secondary non-elastic ply having a right end and a left end and an outer surface and an inner surface, said inner surface having side sections adapted to lie against said outer surface of said primary ply when said belt is wrapped around said body, said left end of said secondary ply overlapping said right end of said primary ply and said right end of said secondary ply overlapping said left end of said secondary ply when said belt is wrapped around said body;
    an elastic tertiary ply fixably attached to a back section of said inner surface of said secondary ply such that said secondary ply is gathered in a first non-tensioned position and cooperates with said secondary ply to provide a second compressional support along said wearer's sacral area when said secondary ply is fully extended around said body.

2. The support belt of claim 1, wherein:
    said outer surface of said primary ply has straps attached generally perpendicular to a longitudinal dimension of said primary ply; and
    said inner surface of said primary ply has an elastic sheet member attached thereto.

3. The support belt of claim 1, further comprising:
    means for detachably fastening said right and left ends of said primary ply.

4. The support belt of claim 1, further comprising:
    means for adjustably overlapping and securing said right end of said secondary ply to said left end of said secondary ply after said secondary ply is fully extended.

5. The support belt of claim 1, wherein said secondary ply and said tertiary ply are fixably attached to said primary ply at a back section of said primary ply.

6. The support belt of claim 2, wherein said secondary ply and said tertiary ply are fixably attached under one of said straps.

7. The support belt of claim 6, wherein said one of said straps is located midway between said right and left ends of said primary ply.

8. The support belt as recited in claim 3, wherein said fastening means is hook and loop fabric.

9. The support belt as recited in claim 4, wherein said securing means is hook and loop fabric.

10. A multi-ply, back and abdominal support belt, comprising:
    a primary elastic ply of a first elastic tension having an outer surface and an inner surface wherein said outer surface has straps attached generally perpendicular to the longitudinal dimension of said primary elastic ply, and said inner surface has an elastic sheet member attached thereto forming a pocket;
    a secondary generally non-elastic ply having an outer surface and an inner surface;
    a tertiary high tension elastic ply of a second elastic tension further comprising separate elastic bands wherein said tertiary high tension elastic ply is fixably attached to said inner surface of said secondary generally non-elastic ply such that said secondary generally non-elastic ply is gathered so as to be non-tensioned in a first position and said secondary generally non-elastic ply and said tertiary elastic ply are fixably attached under one of said straps located midway between said opposing ends of said primary elastic ply; and
    means for detachably fastening opposing ends of said primary elastic ply;
    means for adjustably securing said secondary non-elastic ply to said outer surface of said primary elastic ply.

11. The support belt of claim 10 wherein said tertiary ply further comprises plurality of sets of a multiplicity of sub-bands.

* * * * *